(12) United States Patent
Kojima et al.

(10) Patent No.: US 10,670,586 B2
(45) Date of Patent: Jun. 2, 2020

(54) TEST INSTRUMENT FOR MEASURING ANALYTE IN SAMPLE BY AN AGGREGATION ASSAY USING A METAL COLLOID AND USING A REAGENT ATTACHED IN A DRY STATE IN A REACTION CHAMBER, AND METHOD FOR MEASURING ANALYTE USING SAME

(75) Inventors: Ryo Kojima, Koriyama (JP); Kenta Noda, Koriyama (JP); Yoshiro Sato, Koriyama (JP); Natsuki Sato, Koriyama (JP); Kaduho Ashizawa, Koriyama (JP)

(73) Assignee: NITTO BOSEKI CO., LTD., Fukushima-shi (JP)

( * ) Notice: Subject to any disclaimer, the term of this patent is extended or adjusted under 35 U.S.C. 154(b) by 446 days.

(21) Appl. No.: 13/639,582

(22) PCT Filed: Apr. 4, 2011

(86) PCT No.: PCT/JP2011/058537
§ 371 (c)(1),
(2), (4) Date: Oct. 5, 2012

(87) PCT Pub. No.: WO2011/129220
PCT Pub. Date: Oct. 20, 2011

(65) Prior Publication Data
US 2013/0084651 A1 Apr. 4, 2013

(30) Foreign Application Priority Data
Apr. 14, 2010 (JP) .................. 2010-093142

(51) Int. Cl.
*G01N 33/53* (2006.01)
*G01N 33/553* (2006.01)
(Continued)

(52) U.S. Cl.
CPC .............. *G01N 33/53* (2013.01); *B01L 3/502* (2013.01); *B01L 3/5027* (2013.01);
(Continued)

(58) Field of Classification Search
CPC ...... B01L 3/502; B01L 3/5023; B01L 3/5027; B01L 3/502715; B01L 3/50273;
(Continued)

(56) References Cited

U.S. PATENT DOCUMENTS 4,313,734 A * 2/1982 Leuvering ............ G01N 33/553
422/400
4,756,884 A * 7/1988 Hillman ................ B01F 5/0618
366/DIG. 3
(Continued)

FOREIGN PATENT DOCUMENTS

CN 1502993 A 6/2004
EP 2095123 A2 9/2009
(Continued)

OTHER PUBLICATIONS

Translation of JP 2007/139658; published Jun. 7, 2007.*
(Continued)

*Primary Examiner* — Christopher L Chin
(74) *Attorney, Agent, or Firm* — Kratz, Quintos & Hanson, LLP

(57) ABSTRACT

Disclosed is a test instrument for measuring an analyte in a liquid sample by a noble metal colloid aggregation measurement method. The test instrument involves a reaction chamber in which at least the liquid sample is to be reacted with a reagent, wherein the reagent is adhered on at least a part of a surface constituting the reaction chamber in a dried state, and the reagent enables the measurement of the analyte by a noble metal colloid aggregation measurement method. The test instrument additionally involves a supply section
(Continued)

1: FIRST PLATE
2: PRINTING SURFACE 1
3: PRINTING SURFACE 2
4: SECOND PLATE
5: DRY REAGENT 1
6: INTERMEDIATE PLATE
7: REAGENT SUPPLY UNIT
8: STOPPER
9: MEMBRANE
10: CHANNEL
11: REACTION CHAMBER
12: DRY REAGENT 2 for supplying the liquid sample and a flow path for delivering the liquid sample that has been supplied to the supply section to the reaction chamber, wherein the liquid sample that has been supplied to the supply section is delivered to the reaction chamber through the flow path to cause the liquid sample to be brought into contact with the reagent that has been adhered in a dried state, thereby producing a difference in pressure between the supply section and the reaction chamber for the purpose of dispersing the reagent in the liquid sample. When the test instrument is used, the measurement based on an absorbance at a visible region can be achieved, the analyte can be measured accurately within a short time, and the measurement suitable for a POCT field can be achieved.

16 Claims, 4 Drawing Sheets

(51) Int. Cl.
*G01N 33/543* (2006.01)
*B01L 3/00* (2006.01)
(52) U.S. Cl.
CPC .... *B01L 3/50273* (2013.01); *G01N 33/54313* (2013.01); *G01N 33/54386* (2013.01); *B01L 3/502715* (2013.01); *B01L 2400/0475* (2013.01); *B01L 2400/0487* (2013.01)
(58) Field of Classification Search
CPC ....... B01L 3/502753; B01L 2400/0475; B01L 2400/0487; G01N 33/553; G01N 33/538
USPC .... 422/73, 400, 401, 402; 435/288.4, 288.5, 435/288.7; 436/523, 525, 541
See application file for complete search history.

(56) References Cited

U.S. PATENT DOCUMENTS

| | | | | |
|---|---|---|---|---|
| 4,775,636 | A * | 10/1988 | Moeremans | G01N 33/532 436/518 |
| 5,677,133 | A * | 10/1997 | Oberhardt | G01N 33/54333 435/7.1 |
| 6,143,576 | A * | 11/2000 | Buechler | 436/518 |
| 6,569,674 | B1 * | 5/2003 | McGarry | B01L 3/5027 435/285.1 |
| 6,720,411 | B2 * | 4/2004 | Mirkin | B82Y 15/00 435/6.11 |
| 6,974,669 | B2 * | 12/2005 | Mirkin | C12Q 1/6834 435/5 |
| 2003/0124623 | A1 * | 7/2003 | Yager et al. | 435/7.5 |
| 2003/0127333 | A1 * | 7/2003 | Lauks et al. | 204/600 |
| 2004/0241042 | A1 * | 12/2004 | Pugia et al. | 422/58 |
| 2007/0015140 | A1 * | 1/2007 | Kobori | B01L 3/50825 435/5 |
| 2008/0064232 | A1 | 3/2008 | Reiss et al. | |
| 2009/0325315 | A1 | 12/2009 | Hirai et al. | |
| 2010/0007857 | A1 | 1/2010 | Wang et al. | |
| 2010/0015636 | A1 | 1/2010 | Charlton | |
| 2010/0240148 | A1 * | 9/2010 | Yanagiya | G01N 33/5308 436/501 |

FOREIGN PATENT DOCUMENTS

| | | | |
|---|---|---|---|
| JP | S 59-173760 A | 10/1984 | |
| JP | 04-299262 | 10/1992 | |
| JP | 07-034370 | 2/1995 | |
| JP | 09-196920 | 7/1997 | |
| JP | 10-066861 | 3/1998 | |
| JP | 11-076800 | 3/1999 | |
| JP | 11-080647 | 3/1999 | |
| JP | 2002-245854 | 8/2002 | |
| JP | 2003-254896 | 9/2003 | |
| JP | 2003-254896 A | 9/2003 | |
| JP | 2004-325192 A | 11/2004 | |
| JP | 2005-283250 A | 10/2005 | |
| JP | 2006-292410 A | 10/2006 | |
| JP | 2007-114162 | 5/2007 | |
| JP | 2007-139658 | * 6/2007 | ............ G01N 33/53 |
| JP | 2007-139658 A | 6/2007 | |
| JP | 2007-248101 A | 9/2007 | |
| JP | 2009-192223 A | 8/2009 | |
| JP | 2009-270878 | 11/2009 | |
| JP | 2010-019794 | 1/2010 | |
| JP | 2010-032505 | 2/2010 | |
| JP | 2010-051525 | 3/2010 | |
| JP | 2011-17589 A | 1/2011 | |
| WO | 01/29558 | 4/2001 | |
| WO | 2004/046721 A1 | 6/2004 | |
| WO | 2005/023468 | 3/2005 | |
| WO | 2008/064232 A2 | 5/2008 | |
| WO | WO 2008/127789 A | 10/2008 | |
| WO | WO 2008/146569 A | 12/2008 | |
| WO | 2009/037785 A1 | 3/2009 | |
| WO | WO 2009/072385 A | 6/2009 | |
| WO | 2009/137244 | 11/2009 | |

OTHER PUBLICATIONS

International Search Report for International Application No. PCT/JP2011/058537 dated May 17, 2011.
Extended European Search Report dated Mar. 6, 2014 issued in counterpart application No. 11768741.8.
International Preliminary Examination Report on Patentability (Chapter I) dated Nov. 6, 2012 in counterpart application No. PCT/JP2011/058537.
Japanese Office dated Jan. 15, 2015 in corresponding Japanese Patent Application No. 2012-510620.
Opposition dated Apr. 11, 2016 in the corresponding JP patent application No. 2012-510620 (JP5831448B).
www.cytodiagnostics.com, Apr. 27, 2017, Gold Nanoparticle Properties.

* cited by examiner

1: FIRST PLATE
2: PRINTING SURFACE 1
3: PRINTING SURFACE 2
4: SECOND PLATE
5: DRY REAGENT 1
6: INTERMEDIATE PLATE
7: REAGENT SUPPLY UNIT
8: STOPPER
9: MEMBRANE
10: CHANNEL
11: REACTION CHAMBER
12: DRY REAGENT 2

TEST INSTRUMENT FOR MEASURING ANALYTE IN SAMPLE BY AN AGGREGATION ASSAY USING A METAL COLLOID AND USING A REAGENT ATTACHED IN A DRY STATE IN A REACTION CHAMBER, AND METHOD FOR MEASURING ANALYTE USING SAME

TECHNICAL FIELD

The present invention relates to a test instrument for assaying an analyte in a sample, and a method for assaying an analyte using the same. More specifically, the present invention relates to a test instrument for assaying an analyte in a liquid sample by aggregation assay using a noble metal colloid, which is mainly applied to the clinical test field and, particularly, is capable of rapid and convenient assay at every site such as bed sides of patients or medical emergency sites and suitable for the so-called POCT filed, and a method for assaying an analyte using the same.

BACKGROUND ART

Recent advances in analytical techniques have enabled various biogenic components to be assayed. Particularly, in the clinical test field, various biogenic components in body fluids related to pathological conditions have been assayed with the development of immunoassay based on the principle of specific reaction between antigens and antibodies. In the field of such immunoassay, the point-of-care testing (hereinafter, also referred to as POCT) field has received attention in recent years on the grounds that: a time required from sampling to obtainment of test results can be shortened; an apparatus is convenient; and simple assay can be achieved.

Most of test instruments used in such immunoassay involve BF separation.

An immunochromatography test instrument is known as such a test instrument (Patent Literature 1). In this test instrument used, first antibodies against an analyte that may be present in a sample solution are immobilized, for example, on a sheet as a chromatography medium made of a porous material through which a liquid can be moved by capillarity. The sample solution containing labeled second antibodies, for example, gold colloid-labeled second antibodies, against the analyte is developed from the end of the chromatography medium in the test instrument. Subsequently, a complex of the first antibody, the analyte and the labeled second antibody is captured by the immobilized first antibody site. Since unreacted labeled antibodies are moved to downstream, color derived from the gold colloid or the like is observed at the immobilized antibody site only when the analyte is present in the sample. In the first place, this method merely determines the presence or absence of the analyte by the visual observation of the presence or absence of color derived from the gold colloid or the like and is disadvantageously incapable of quantitative assay.

Alternatively, a test instrument for analyte quantification is also known, in which a sample is transported via a spatial channel by pump suction (Patent Literature 2). This instrument comprises a sample supply port, a sample treatment chamber provided with labeled antibodies, an assay chamber provided with immobilized antibodies, a waste liquid chamber and a pump connecting port, wherein these members are communicated with each other via channels. A sample is applied to the sample supply port and transported by suction to the sample treatment chamber in which the labeled antibodies are in turn liberated and reacted with the analyte in the sample. Subsequently, the sample is transported by suction again to the assay chamber in which a conjugate of the immobilized antibody, the analyte and the labeled antibody is in turn formed and stopped for a given time. Components other than the analyte in the sample are transported into the waste liquid chamber by suction. Then, the analyte contained in the sample can be assayed quantitatively by the photometry of the analyte-derived conjugate located in the assay chamber. This instrument, however, is relatively difficult to control due to several stages of sample transport using a pump, and the assay results are disadvantageously largely influenced by conditions.

A method for solving these problems is also known, in which a channel-openable/closable occlusion member is combined with pump pressurization under the similar assay principle (Patent Literature 3). This method, however, requires the undesirably complicated structure of a test instrument.

Meanwhile, development examples of test instruments capable of quantifying an analyte through latex immunoagglutination reaction without the need of BF separation are also known, although few in number in the POCT field (Patent Literature 4). This method involves incorporating antibody-sensitized latex or the like in a dry state to a test instrument. In such a case, a liquid reagent must be produced in advance by time-consuming complicated freeze drying, not by simple natural drying. In the first place, antibody-sensitized particles are not completely dissolved in water but are merely dispersed therein. Thus, this method has the disadvantage that the dried antibody-sensitized particles are hardly redispersed. Unlike the method involving BF separation, the method based on the latex immunoagglutination reaction requires completely redispersing antibody-sensitized particles. Therefore, in the case of using latex immunoagglutination assay in dry chemistry, immunoassay must be performed by the application of spatial processing means such as rotation or shaking for latex redispersion. As a result, a test instrument used therein disadvantageously tends to be complicated.

CITATION LIST

Patent Literature

Patent Literature 1: JP 4-299262 A
Patent Literature 2: JP 9-196920 A
Patent Literature 3: JP 2009-270878 A
Patent Literature 4: JP 2007-114162 A

SUMMARY OF INVENTION

Technical Problem

An object of the present invention is to provide a convenient test instrument which is capable of accurately assaying an analyte in a sample by dry chemistry, and a method for assaying an analyte, which is capable of assay in a short time using the same, wherein the test instrument and the assay method are suitable for the POCT field. A further object of the present invention is to provide a test instrument which is capable of assay based on absorbance in the visible region and as such, can be applied to an apparatus using a general-purpose visible spectrophotometer and can accurately assay an analyte, and an assay method using the same.

Solution to Problem

Under such circumstances, the present inventors have studied to develop a convenient test instrument capable of assaying an analyte. Consequently, the present inventors have found that: a noble metal colloid is used as particles to be sensitized with an antibody, and this reagent is attached to a reaction chamber in a test instrument having a channel system and dried, whereby the dry reagent is easily redispersed by pressurization to an extent that blood cells are removed from whole blood using a blood cell separating membrane; and as a result, an analyte can be assayed accurately without rotating operation or other spatial movement processing means such as shaking. The present invention has been completed by further studies based on these findings.

Specifically, the present invention relates to:

[1] a test instrument for assaying an analyte in a liquid sample by aggregation assay using a noble metal colloid, the test instrument comprising at least a reaction chamber in which the liquid sample is reacted with a reagent, wherein the reagent is attached in a dry state to at least a portion of a surface constituting the reaction chamber and is a reagent capable of assaying the analyte by the aggregation assay using a noble metal colloid, and further comprising: a supply unit for supplying the liquid sample; and a channel for transporting the liquid sample supplied to the supply unit into the reaction chamber, wherein the test instrument is capable of generating a pressure difference between the supply unit and the reaction chamber by which the liquid sample supplied to the supply unit is transported into the reaction chamber via the channel and contacted with the reagent attached thereto in a dry state to disperse the reagent in the liquid sample;

[2] the test instrument according to [1], wherein the reagent capable of assaying the analyte by the aggregation assay using a noble metal colloid is a reagent containing a noble metal colloid sensitized with a partner specifically binding to the analyte or a reagent containing the partner and a noble metal colloid sensitized with the same substance as the analyte;

[3] the test instrument according to [1] or [2], wherein the reaction chamber is provided with a first plane surface, a second plane surface facing the first plane surface, and a third surface being in contact with both the first plane surface and the second plane surface and defining a space between the first plane surface and the second plane surface, wherein the reagent containing a noble metal colloid sensitized with a partner specifically binding to the analyte is attached in a dry state to the first plane surface or the second plane surface facing the first plane surface, or wherein in the reagent containing the partner and a noble metal colloid sensitized with the same substance as the analyte, the partner is attached in a dry state to either the first plane surface or the second plane surface facing the first plane surface while the noble metal colloid sensitized with the same substance as the analyte is attached in a dry state to the other plane surface;

[4] the test instrument according to any of [1] to [3], wherein the noble metal colloid is a gold colloid or a palladium colloid;

[5] the test instrument according to any of [1] to [4], wherein the channel and the reaction chamber are connected to an outside of the test instrument via an air-permeable and liquid-impermeable porous membrane;

[6] the test instrument according to any of [1] to [5], wherein the pressure difference is generated by pressurization;

[7] the test instrument according to any of [1] to [6], wherein the test instrument is capable of pressurizing the liquid sample supplied to the supply unit by means of a pressurization unit and transporting the resulting sample into the reaction chamber;

[8] the test instrument according to any of [1] to [7], wherein the liquid sample is a biological sample, and the analyte is a biogenic component;

[9] the test instrument according to any of [1] to [8], further comprising, between the supply unit and the channel, a membrane for separating a solid from the liquid sample;

[10] a method for assaying an analyte in a liquid sample, comprising supplying a liquid sample suspected of containing the analyte to the supply unit in a test instrument according to any of [1] to [9], subsequently generating a pressure difference between the supply unit and the reaction chamber by which the liquid sample is transported into the reaction chamber via the channel and contacted with the reagent in the reaction chamber to disperse the reagent in the liquid sample, reacting the analyte in the liquid sample with the reagent, irradiating the obtained mixed solution with light, and assaying the analyte in the liquid sample on the basis of change in absorbance derived from transmitted light or reflected light;

[11] the assay method according to [10], wherein the irradiation of the mixed solution with light comprises irradiating the reaction chamber with light;

[12] the assay method according to [10] or [11], wherein the light used in the irradiation has a wavelength in the range of 340 to 800 nm;

[13] the assay method according to [12], wherein the light used in the irradiation has a wavelength in the range of 390 to 420 nm; and

[14] an apparatus for assaying an analyte in a liquid sample, comprising a test instrument according to any of [1] to [9] in combination with a visible spectrophotometer for irradiating the reaction chamber with light and reading transmitted light or reflected light.

Advantageous Effects of Invention

According to the present invention, an analyte in a liquid sample can be assayed accurately by dry chemistry using a convenient test instrument. Furthermore, the test instrument and the assay method of the present invention are capable of assay based on absorbance in the visible region and as such, can be applied to an apparatus using a general-purpose visible spectrophotometer and can accurately assay an analyte in a short time. The test instrument and the assay method of the present invention are suitable for the POCT field.

DESCRIPTION OF EMBODIMENTS

Figure 1:
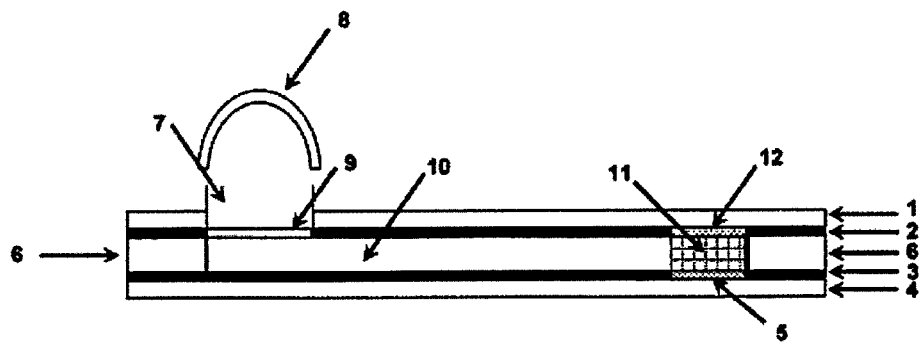
FIG. 1 is a vertical sectional view showing one example of a test instrument used in the present invention.

The assay method of the present invention is based on the technique of dry chemistry. In the present specification, the dry chemistry refers to an assay format in which a liquid sample is added to a reagent for analyte assay prepared in advance in a dry state in a test instrument to disperse the reagent with water in the sample as a solvent so that the liquid sample and the dispersed reagent are reacted in the reaction chamber of the test instrument.

The test instrument of the present invention is a test instrument for assaying an analyte in a liquid sample by aggregation assay using a noble metal colloid, the test instrument comprising at least a reaction chamber in which the liquid sample is reacted with a reagent, wherein the reagent is attached in a dry state to at least a portion of a surface constituting the reaction chamber and is a reagent capable of assaying the analyte by the aggregation assay using a noble metal colloid, for example, a reagent containing a noble metal colloid sensitized with a partner specifically binding to the analyte or a reagent containing the partner and a noble metal colloid sensitized with the same substance as the analyte, and further comprising: a supply unit for supplying the liquid sample; and a channel for transporting the liquid sample supplied to the supply unit into the reaction chamber, wherein the test instrument is capable of generating a pressure difference between the supply unit and the reaction chamber by which the liquid sample supplied to the supply unit is transported into the reaction chamber via the channel and contacted with the reagent attached thereto in a dry state to disperse the reagent in the liquid sample.

The test instrument of the present invention comprises, for example: a supply unit for supplying the liquid sample; a reaction chamber which is disposed in the test instrument and in which the liquid sample is reacted with a reagent; and a channel for transporting the liquid sample supplied to the supply unit into the reaction chamber, wherein:

the channel and the reaction chamber are connected to an outside of the test instrument via an air-permeable and liquid-impermeable porous membrane;

the reaction chamber is provided with a first plane surface, a second plane surface facing the first plane surface, and a third surface being in contact with both the first plane surface and the second plane surface and defining a space between the first plane surface and the second plane surface;

the channel and the reaction chamber are connected by an interconnecting hole disposed in the third surface;

the reagent is attached in a dry state to at least one of the plane surfaces; and the test instrument pressurizes the liquid sample supplied to the supply unit by means of a pressurization unit disposed in the supply unit and transports the resulting sample into the reaction chamber.

The liquid sample according to the present invention may be any of those containing a liquid and is preferably a biological sample. Examples thereof can include blood samples, urine and spinal fluids.

Examples of the blood samples can include serum, plasma and whole blood. It is preferred that the test instrument of the present invention should further comprise, between the supply unit and the channel, a membrane for separating a solid from the liquid sample. Particularly, when the liquid sample is whole blood or the like and contains solid components such as blood cells, it is preferred for solid-liquid separation that the test instrument of the present invention should further comprise, between the supply unit and the channel, a membrane for separating a solid from the liquid sample.

In the case of using the membrane, the liquid sample is applied to the supply unit, and only the liquid sample is then sent into the reaction chamber via the channel while membrane separation, for example, the separation and removal of solid components such as blood cells, is performed by use of a pressure difference, preferably, pressing force. As a result, the liquid sample is dissolved by collision with the reagent attached thereto in a dry state to disperse the noble metal colloid in the liquid sample. Thus, the analyte in the liquid sample can be assayed by the aggregation method using a noble metal colloid. Since whole blood is generally rich in complicated biogenic components and solid components such as blood cells, it is usually difficult to accurately assay only an analyte therein. In the present invention, however, use of membrane separation based on a pressure difference allows assay of an analyte in whole blood, which can be collected easily from, for example, the tip of a finger, without diluting the whole blood. Thus, the test instrument of the present invention has the advantage that the liquid sample can be applied thereto without being diluted with a reagent or the like. Specifically, when the liquid sample is a biological sample such as a blood sample, use of a noble metal colloid or the like in the present invention allows assay of an analyte without diluting the sample, in spite of the fact that the colloid is hardly dispersed in the sample due to the high viscosity of the sample.

In the present specification, the aggregation assay using a noble metal colloid refers to a method using a noble metal colloid instead of latex in latex agglutination assay and involving, for example, mixing a sample with a noble metal colloid reagent sensitized with a particular component to cause aggregation reaction and assaying the analyte on the basis of the degree of the aggregation.

The reagent according to the present invention is not particularly limited as long as it is a reagent capable of assaying the analyte by the aggregation assay using a noble metal colloid.

Examples of such a reagent can include a reagent containing a noble metal colloid sensitized with a partner specifically binding to the analyte and a reagent containing the partner and a noble metal colloid sensitized with the same substance as the analyte. Examples of the partner specifically binding to the analyte can include an antibody against an antigen serving as the analyte and an antigen against an antibody serving as the analyte. Examples of other combinations of the analyte and the partner specifically binding thereto include combinations of biotin with avidin or streptavidin, lectin with a lectin-binding sugar, a hormone with a hormone receptor, a cytokine with a cytokine receptor, protein A with IgG, and DNA or RNA with DNA or RNA complementary thereto.

Hereinafter, the reagent will be described by taking, as an example, the case where the analyte is an antigen such as CRP or cystatin C and its partner is an antibody such as an anti-CRP antibody or an anti-cystatin C antibody. In the case of using an antibody as the analyte, the antigen and the antibody may be reversed in the description below.

When a noble metal colloid sensitized with a partner (antibody) specifically binding to the analyte (antigen) is used as the reagent, an immunoagglutination complex (antigen-antibody complex) formed during reaction becomes bigger according to the amount of the analyte (antigen). The concentration of the analyte (antigen) can be determined from the size.

On the other hand, when a reagent containing both the partner (antibody) and a noble metal colloid sensitized with the same substance (antigen) as the analyte (antigen) is used as the reagent, an immunoagglutination complex (antigen-antibody complex) formed during reaction becomes smaller according to the amount of the analyte (antigen). This method is generally called immunoagglutination inhibition and involves causing the aggregation reaction between the antigen that has sensitized the noble metal colloid in the reagent and the antibody in the reagent. In this method, the antigen sample entering the assay system inhibits the aggregation reaction between the antigen-sensitized noble metal colloid and the antibody in the reagent, resulting in a smaller agglutination complex and a decreased amount thereof.

When a combination of, for example, biotin with avidin or streptavidin, lectin with a lectin-binding sugar, a hormone with a hormone receptor, a cytokine with a cytokine receptor, protein A with IgG, or DNA or RNA with DNA or RNA complementary thereto is used as the analyte and the partner specifically binding thereto, the analyte can also be assayed by the aggregation assay using a noble metal colloid in the same way as in the combination of the antigen or the antibody with the antibody or the antigen.

The reagent used in the present invention may be supplemented with an excipient, a stabilizer, a buffer, and a surfactant.

Examples of the excipient can include proteins such as albumin, amino acids such as glycine, alcohols such as mannitol, and hydrocarbon compounds such as glucose.

The stabilizer is generally preferably a substance easily carrying water in the molecule, for example, a sugar such as sorbitol.

The substance-sensitized noble metal colloid reagent, such as an antibody-sensitized noble metal colloid or an antigen-sensitized noble metal colloid, used as the reagent in the present invention, can be prepared, for example, as follows: a sensitizing substance such as an antibody is added to a noble metal colloid solution, which is in turn adjusted with a buffer solution, left standing at room temperature, and then supplemented with a BSA coating solution. Subsequently, the mixture is centrifuged, and the supernatant is discarded while the precipitate is collected. This precipitate is suspended by the addition of a BSA coating solution thereto and completely dispersed by ultrasonication. After centrifugation, the obtained precipitate is suspended by the addition of a suspending solution to obtain a substance-sensitized noble metal colloid. Subsequently, sorbitol, a surfactant, and the like are added to the obtained substance-sensitized noble metal colloid, and other necessary components can be optionally added thereto to prepare a reagent capable of assaying the analyte by the aggregation assay using a noble metal colloid.

For the production of the test instrument of the present invention, the reagent capable of assaying the analyte by the aggregation assay using a noble metal colloid is attached in a dry state to at least a portion of a surface constituting the reaction chamber. In this case, for example, the reagent in a liquid state can be applied to at least a portion of a surface constituting the reaction chamber and subsequently dried. Examples of the drying of the liquid reagent include natural drying and freeze drying. Unlike a latex reagent, a natural drying method is preferable for the present invention in terms of reagent stability.

The reagent for analyte assay may be attached in one portion in a dry state to a surface constituting the reaction chamber in the test instrument. Alternatively, the reagent may be divided, in consideration of reagent stability, etc., into two portions, which are in turn attached to the first plane surface and the second plane surface, respectively. When a reagent containing a partner against the analyte and a noble metal colloid sensitized with the same substance as the analyte is used as the reagent, it is preferred that the reagent should be attached in two portions in a dry state to the first plane surface and the second plane surface, respectively.

The aggregation assay typically employs latex particles, whereas a noble metal colloid is used in the present invention. Examples of the noble metal used in the noble metal colloid can include gold, silver, platinum and palladium. Gold, silver or palladium is preferable, and gold or palladium is more preferable with gold further preferred. This is because use of the test instrument of the present invention using a gold colloid or a palladium colloid, particularly, a gold colloid, allows very accurate assay of the analyte. The maximum absorption wavelength of the gold colloid is 500 nm or larger. When the gold colloid is used as the noble metal colloid in the present invention, a mixed solution obtained after aggregation reaction such as immunoagglutination reaction may be irradiated with light at a wavelength of 390 to 420 nm so that the analyte in the liquid sample is assayed on the basis of change in absorbance derived from transmitted light or reflected light. Alternatively, the maximum absorption wavelength of the palladium colloid is 250 nm or smaller. When the palladium colloid is used as the noble metal colloid in the present invention, a mixed solution obtained after aggregation reaction such as immunoagglutination reaction may be irradiated with light at a wavelength of 390 to 420 nm so that the analyte in the liquid sample is assayed on the basis of change in absorbance derived from transmitted light or reflected light. This case is preferable because a light source (LED) for light irradiation is easily obtainable.

In the present invention, the particle size of the noble metal colloid is usually 1 to 200 nm, preferably 20 to 150 nm. It is preferred that the noble metal colloid should be dispersed easily upon contact or collision with the liquid sample by a pressure difference. The fine noble metal particles may be protected with a protecting component.

Such a noble metal colloid is not particularly limited as long as it can be dispersed upon contact with the liquid sample by a pressure difference according to the present invention. Examples thereof can include a complex compound of a noble metal in a quaternary ammonium salt form (JP 2001-192712 A), a noble metal colloid protected with a polymer pigment dispersant (JP 11-76800 A and JP 11-80647 A), a noble metal colloid with sodium citrate as a dispersant (JP 10-66861 A), a noble metal colloid protected with an oxide of a peptide or an oxide of a glucosamine compound (International Publication No. WO2005/023468), and a noble metal colloid protected with a compound having an amino group and a carboxyl group, such as an amino acid (JP 2002-245854 A).

For achieving the pressure difference according to the present invention, it is preferred that the channel and the reaction chamber should be connected to an outside of the test instrument via an air-permeable and liquid-impermeable porous membrane.

In the present invention, means for generating the pressure difference may be any means which can generate a pressure difference between the reaction chamber and the supply unit by which the liquid sample is sent from the supply unit into the reaction chamber via the channel to disperse the dry reagent therein. Specific examples thereof can include pressurization means and pressure reduction means. It is preferred to use pressurization means because the resulting test instrument has a simple structure. Specifically, it is preferred that the test instrument should be capable of pressuring the sample supplied to the supply unit by means of a pressurization unit disposed in the supply unit and transporting the resulting sample into the reaction chamber.

When pressure reduction means is used in the present invention, gas in the reaction chamber is pulled out, for example, using a pump through a gas-permeable and liquid-impermeable membrane or substance to generate a pressure difference.

For the present invention, it is preferred that the irradiation of the mixed solution with light should comprise irradiating the reaction chamber with light. It is therefore preferred that the upper and lower surfaces of the reaction chamber should be transparent. Specifically, it is preferred that the reaction chamber should also serve as an assay chamber.

In this case, the reaction chamber is irradiated for the irradiation of the mixed solution with light, and it is thus preferred to use a visible spectrophotometer. It is therefore preferred that at least a portion of the upper and lower surfaces of the reaction chamber should be transparent. In this case, change in absorbance after reaction can be determined using a visible spectrophotometer for reading change in absorbance derived from transmitted light or reflected light by light irradiation from above, and the analyte can be quantified on the basis of increase or decrease in the change.

The assay method of the present invention may use an apparatus comprising two members: the test instrument of the present invention in combination with a visible spectrophotometer for irradiating the reaction chamber with light and reading transmitted light or reflected light. This apparatus may have, for example, a pump constituting pressurization means for pressurizing the supply unit.

The assay method of the present invention uses the test instrument of the present invention described above in detail and is a method for assaying an analyte in a liquid sample, comprising supplying the liquid sample to the supply unit in the test instrument of the present invention, subsequently generating a pressure difference between the supply unit and the reaction chamber by which the liquid sample is transported into the reaction chamber via the channel and contacted with the reagent in the reaction chamber to disperse the reagent in the liquid sample, reacting the analyte in the liquid sample with the reagent, irradiating the obtained mixed solution with light, and assaying the analyte in the liquid sample on the basis of change in absorbance derived from transmitted light or reflected light.

In the present invention, the state of the sensitized noble metal colloid is changed through antigen-antibody reaction or the like. As a result, change in absorbance derived from transmitted light or reflected light occurs between before and after reaction upon light irradiation. Data before reaction can be determined using an analyte-free sample as the sample. The concentration of the analyte can be determined from the difference in absorbance between before and after reaction.

For the assay method of the present invention, it is preferred that the light used in the irradiation should have a wavelength of 340 to 800 nm, more preferably 390 to 420 nm. This is because a light source of 390 to 420 nm is versatile for use in dry chemistry.

Hereinafter, assay of an antigen analyte will be described by taking, as an example, the case using an antibody-sensitized noble metal colloid (in the case of antibody assay, the antigen and the antibody may be reversed in the description below). When the noble metal colloid is a gold colloid, the maximum absorption wavelength of the antibody-sensitized gold colloid solution (reagent) is usually 500 nm or larger. The antibody-sensitized gold colloid solution causes large change in absorbance through reaction with its antigen (analyte) around the maximum absorption wavelength. On the other hand, the antibody-sensitized gold colloid solution causes change in absorbance through reaction with the antigen even at 390 to 420 nm. Alternatively, when the noble metal colloid is a palladium colloid, the maximum absorption wavelength of the antibody-sensitized palladium colloid solution is usually 250 nm or smaller. The antibody-sensitized palladium colloid solution causes large change in absorbance through reaction with its antigen around this maximum absorption wavelength or causes change in absorbance through reaction with the antigen even at 390 to 420 nm. In the present invention, the concentration of the antigen can be determined from the degree of change in absorbance caused by the reaction of the liquid sample with the reagent, such as antigen-antibody reaction.

When other combinations are used as the analyte and the partner specifically binding thereto, the analyte can also be assayed by the aggregation assay using a noble metal colloid in the same way as above.

In the reaction chamber, the reagent can be dissolved in the liquid sample and reacted therewith, for example, at 20 to 40° C., preferably around 37° C.

The assay method of the present invention can be carried out without applying rotating operation or shaking operation to the test instrument, i.e., without particularly spatially moving the test instrument. Specifically, in the present invention, the dry reagent can be dispersed and reacted through immunoreaction or the like without particularly applying, to the test instrument, external physical movement or operation other than the generation of a pressure difference between the supply unit and the reaction chamber in the test instrument and without moving the test instrument itself. In addition, the assay method of the present invention does not require BF separation. As a result, the analyte in the sample can be assayed accurately using an exceedingly simple test instrument.

Hereinafter, the assay method of the present invention and the test instrument used therein will be described more specifically with reference to the drawings.

Figure 2:
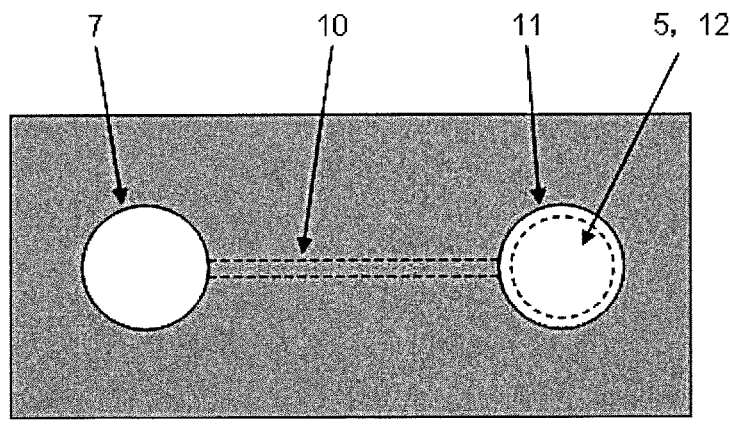
FIG. 2 is a top view showing one example of the test instrument used in the present invention.
Figure 3:
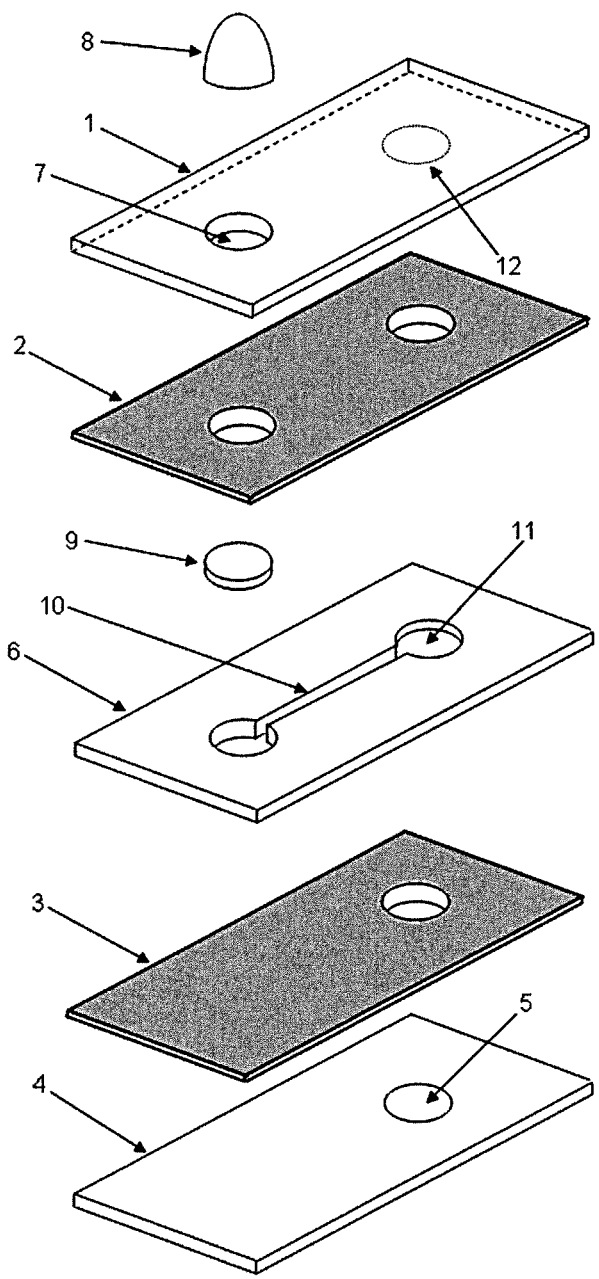
FIG. 3 is an exploded perspective view showing one example of the test instrument used in the present invention.

A test instrument will be described with reference to the drawings as a preferable embodiment of the test instrument according to the present invention. FIG. 1 is a vertical sectional view of the test instrument. FIG. 2 is a top view of the test instrument. FIG. 3 is an exploded perspective view of the test instrument.

The test instrument, as shown in FIGS. 1 to 3, has an integrated structure in which a first plate 1, a printing surface 1 (represented by reference number 2 in the drawings), an intermediate plate 6 composed of a porous membrane, a printing surface 2 (represented by reference number 3 in the drawings) and a second plate 4 are stacked in the vertical direction. A round sample supply unit 7 is disposed in the first plate 1 on the upper layer side. In this context, each printing surface is a black-painted layer. The testing instrument is configured such that a depression is disposed in a site to be coated with a dry reagent due to the absence of the printing surface and can be coated with the dry reagent. The printing surface 1 (printing surface 2) may be formed by coating, screen printing, or the like on one side of the first plate 1 (second plate 4) or the intermediate plate 6, or may be formed as a film independent of these plates and then stacked between these plates. A bottomed cylindrical stopper 8 is removably attached in the neighborhood of the upper region of the sample supply unit 7. An easily processable resin material, for example, a styrene-acrylonitrile resin (ABS resin), is used in the first plate 1 and the second plate 4. A liquid-impermeable and air-permeable porous material, for example, an ethylene tetrafluoride resin (PTFE resin), is used in the intermediate plate 6.

The intermediate plate 6 is disposed between the first plate 1 and the second plate 4 and bonded thereto via the printing surface 1 (represented by 2) and the printing surface 2 (represented by 3). The intermediate plate 6 is provided with a channel 10 for liquid reagents and further provided with a reaction chamber 11 communicating with the channel 10. An air-permeable and liquid-permeable porous membrane 9 is disposed between the sample supply unit 7 and the channel 10.

A predetermined amount of a reagent is applied to either the first plane surface or the second plane surface, or both, of the reaction chamber 11, and attached in a dry state thereto to form a dry reagent 1 (represented by reference number 5 in the drawings) and/or a dry reagent 2 (represented by reference number 12 in the drawings).

In the case of actual assay, a liquid sample is supplied from the sample supply unit 7. Then, the sample supply unit 7 is covered with the stopper 8, which is in turn pressurized, for example, with a finger. As a result, air in the reaction chamber 11 or the channel 10 is discharged from the intermediate plate 6 to the outside so that the liquid sample is sent into the reaction chamber 11. Since the reagent is attached in a dry state to either the first plane surface or the second plane surface, or both, of the reaction chamber 11, when the liquid sample is delivered into the space of the reaction chamber 11, the reagent is dispersed in the liquid sample to start the reaction of the liquid sample with the reagent. The sample and the reagent are mixed in one space and thus, uniformly mixed.

After the reaction of the liquid sample with the reagent in the reaction chamber 11, the mixed solution can be assayed using transmitted light or reflected light. For the optical assay using transmitted light or reflected light, the first plate 1 and the second plate 4 are wholly made of a light transmissive resin. After the reaction of the liquid sample with the reagent in the reaction chamber 11, the mixed solution can be exposed to, for example, transmitted light having a wavelength of 405 nm, for example, by irradiation toward the first plate 1 from below the second plate 4, and assayed on the basis of the absorption of the transmitted light in the reaction chamber 11.

EXAMPLES

Hereinafter, the present invention will be described in more detail with reference to Examples and Comparative Examples. However, the present invention is not intended to be limited to these examples.

Example 1

Method for Assaying Human CRP Using Gold Colloid According to the Present Invention 1. Method
1) Preparation of Anti-Human CRP Antibody-Sensitized Gold Colloid A gold colloid was sensitized with an anti-human CRP antibody as follows:

10 mL of a solution containing an anti-human CRP antibody adjusted to 0.2 mg/mL with a Tris buffer solution was added to 10 mL of a gold colloid solution (sold by Nacalai Tesque, Inc., protected gold colloid solution) having an average particle size of 50 nm, and the mixture was left standing at room temperature for 15 minutes and then supplemented with 10 mL of a BSA coating solution. Subsequently, the mixture was centrifuged at 15,000 rpm for 10 minutes, and the supernatant was discarded while the precipitate was collected. This precipitate was suspended by the addition of 20 mL of a BSA coating solution thereto and completely dispersed by ultrasonication for 30 seconds. After centrifugation, the obtained precipitate was suspended by the addition of 1 mL of a suspending solution to obtain an anti-human CRP antibody-sensitized gold colloid.

2) Preparation of Dry Reagent

Sorbitol and a surfactant were added at final concentrations of 2% and 0.1%, respectively, to the anti-human CRP antibody-sensitized gold colloid obtained above in 1).

3) Preparation of Test Instrument and Operation Thereof

The reagent thus prepared was applied in amounts of 0.375 µL and 0.5 µL onto two PET sheets, respectively, and left for natural drying. A sheet having a sample channel was sandwiched between the coated sheets thus dried, and bonded thereto to prepare a test instrument configured as shown in FIGS. 1 to 3. A sample was introduced in an amount of 1 part by volume in 2.5 parts by volume in terms of the volume of a reaction cell to the supply unit and introduced to the reaction chamber via the channel by use of pressing force to dissolve the reagent therein. For assay, the sample thus introduced was reacted at 37° C. for 10 minutes, and absorbance after the reaction was determined by the photometry of the reagent-coated site at a wavelength of 405 nm.

The reagent and sample used were specifically as follows:
Reagent for Gold Colloid Preparation:
BSA Coating Solution

| | |
|---|---|
| Tris | 10 mM pH 9.2 |
| BSA (bovine serum albumin) | 1.0% |
| PEG (average molecular weight: 20,000) | 0.1% |

Tris Buffer Solution

| | |
|---|---|
| Tris | 10 mM pH 9.2 |

Suspending Solution

| | |
|---|---|
| Tris | 100 mM pH 9.2 |

Sample:
Sera (n=30) from humans who gave informed consent were used.

4) Assay Using Test Instrument

Correlation with the existing method (latex method) was confirmed using sera (n=30) from humans who gave informed consent.

For the correlation confirmation, the assay was conducted using N-Assay LA CRP D-type (manufactured by Nittobo Medical Co., Ltd.) as the existing method and Hitachi automatic analyzer model 7180. Also, a calibration curve for the dry reagent was prepared using control serum having a known CRP concentration.

2. Results

Figure 4:
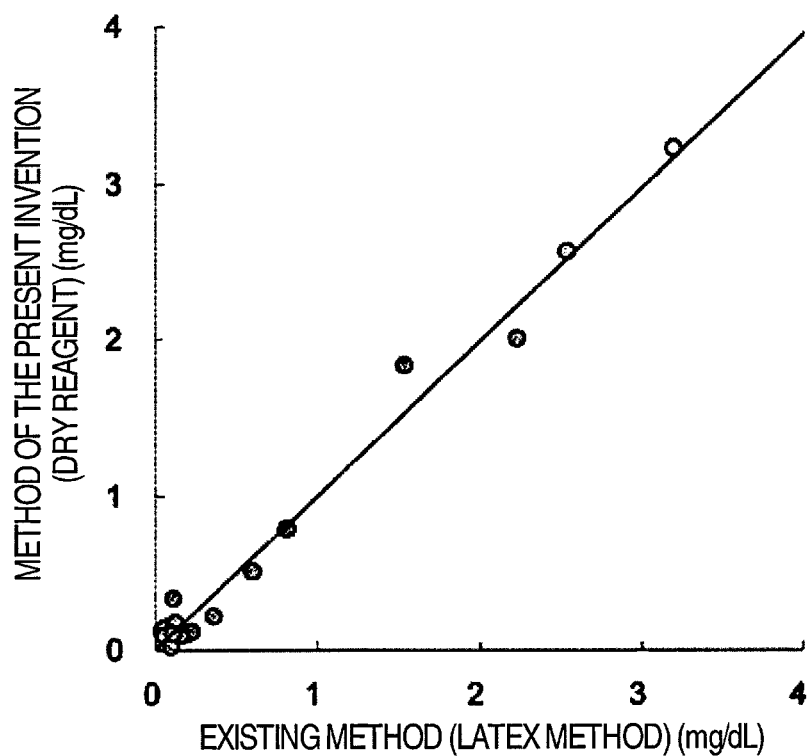
FIG. 4 is a diagram showing the correlation of human CRP assay between the assay method of the present invention based on dry chemistry using a gold colloid and an assay method based on the existing liquid reagent method.

Correlation was confirmed by plotting the existing method on the X-axis and the method of the present invention on the Y-axis. As shown in FIG. 4, the favorable results of Y=0.9849X+0.007 with a correlation coefficient of 0.9925 were obtained. This shows that the assay method of the present invention can accurately assay human CRP using a gold colloid.

Example 2

Method for Assaying Human Cystatin C Using Gold Colloid According to the Present Invention 1. Method
1) Preparation of Anti-Human Cystatin C Antibody-Sensitized Gold Colloid A gold colloid was sensitized with an anti-human cystatin C antibody as follows: 3 mL of a solution containing an anti-human cystatin C antibody adjusted to 150 µg/mL with a Tris buffer solution was added to 9 mL of a gold colloid solution (manufactured by Winered Chemical Corp.) having an average particle size of 50 nm, and the mixture was left standing at room temperature for 15 minutes and then supplemented with 9 mL of a BSA coating solution. Subsequently, the mixture was centrifuged at 15,000 rpm for 10 minutes, and the supernatant was discarded while the precipitate was collected. This precipitate was suspended by the addition of 9 mL of a BSA coating solution thereto and completely dispersed by ultrasonication for 30 seconds. After centrifugation, the obtained precipitate was suspended by the addition of 705 µL of a suspending solution to obtain an anti-human cystatin C antibody-sensitized gold colloid.

2) Preparation of Dry Reagent

Sorbitol and a surfactant were added at final concentrations of 2% and 0.1%, respectively, to the anti-human cystatin C antibody-sensitized gold colloid obtained above in 1).

3) Preparation of Test Instrument and Operation Thereof

The reagent thus prepared was applied to in amounts of 0.375 µL and 0.5 µL onto two PET sheets, respectively, and dried. A sheet having a sample channel was sandwiched between the coated sheets thus dried, and bonded thereto. A sample was introduced in an amount of 1 part by volume in 2.5 parts by volume in terms of the volume of a reaction cell to dissolve the reagent therein. For assay, the sample thus introduced was reacted at 37° C. for 7 minutes, and absorbance after the reaction was determined by the photometry of the reagent-coated site at wavelengths of 405 nm and 800 nm.

The reagent and sample used were specifically as follows:
Reagent for Gold Colloid Preparation:
BSA Coating Solution

| Tris | 10 mM pH 9.2 |
|---|---|
| BSA (bovine serum albumin) | 1.0% |
| PEG (average molecular weight: 20,000) | 0.1% |

Tris Buffer Solution

| Tris | 10 mM pH 9.2 |
|---|---|

Suspending Solution

| Tris | 100 mM pH 9.2 |
|---|---|

Sample:
Sera (n=28) from humans who gave informed consent were used.

4) Assay Using Test Instrument

Correlation with the existing method (latex method) was confirmed using sera (n=28) from humans who gave informed consent.

For the correlation confirmation, the assay was conducted using N-Assay LA cystatin C (manufactured by Nittobo Medical Co., Ltd.) as the existing method and Hitachi automatic analyzer model 7180. Also, a calibration curve for the dry reagent was prepared using control serum having a known cystatin C concentration.

2. Results

Figure 5:
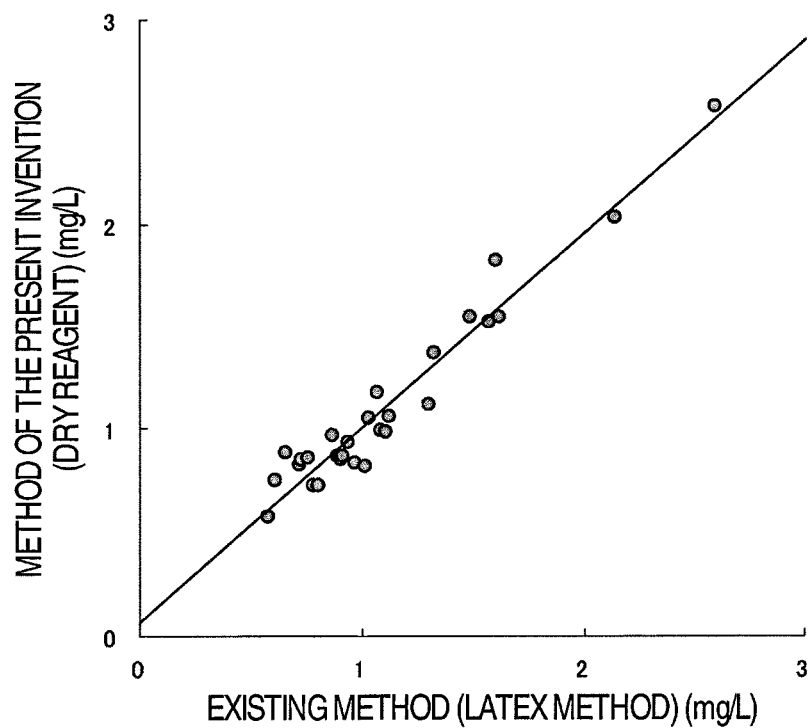
FIG. 5 is a diagram showing the correlation of human cystatin C assay between the assay method of the present invention based on dry chemistry using a gold colloid and an assay method based on the existing liquid reagent method.

Correlation was confirmed by plotting the existing method on the X-axis and the method of the present invention on the Y-axis. As shown in FIG. 5, the favorable results of Y=0.9429X+0.0635 with a correlation coefficient of 0.9710 were obtained. This shows that the assay method of the present invention can accurately assay human cystatin C using a gold colloid.

Example 3

Method for Assaying Human CRP Using Palladium Colloid According to the Present Invention 1. Method
1) Preparation of Anti-Human CRP Antibody-Sensitized Palladium Colloid A palladium colloid was sensitized with an anti-human CRP antibody as follows:

8 mL of a solution containing an anti-human CRP antibody adjusted to a protein concentration of 0.2 mg/dL with a Tris buffer solution was added to 8 mL of a palladium colloid solution (manufactured by Winered Chemical Corp.) having an average particle size of 76 nm, and the mixture was left standing at room temperature for 15 minutes, then supplemented with 8 mL of a BSA coating solution, and left standing for 15 minutes. Subsequently, the mixture was centrifuged at 15,000 rpm for 20 minutes, and the supernatant was discarded while the precipitate was collected. This precipitate was suspended by the addition of 16 mL of a BSA coating solution thereto and completely dispersed by ultrasonication for 60 seconds. After centrifugation at 15,000 rpm for 20 minutes, the obtained precipitate was suspended by the addition of 600 µL of a suspending solution to obtain an anti-human CRP antibody-sensitized palladium colloid.

2) Preparation of Dry Reagent

Glucose and a surfactant were added at final concentrations of 2% and 0.6%, respectively, to the anti-human CRP antibody-sensitized palladium colloid obtained above in 1).

3) Preparation of Test Instrument and Operation Thereof

The reagent thus prepared was applied to in an amount of 0.5 µL onto one PET sheet and dried. A sheet having a sample channel was sandwiched between the reagent-coated PET sheet thus dried and another PET sheet (uncoated), and bonded thereto. A sample was introduced in an amount of 1 part by volume in 2.5 parts by volume in terms of the volume of a reaction cell to dissolve the reagent therein. For assay, the sample thus introduced was reacted at 37° C. for 10 minutes, and absorbance after the reaction was determined by the photometry of the reagent-coated site at a wavelength of 405 nm.

The reagent and sample used were specifically as follows:
Reagent for Palladium Colloid Preparation:
BSA Coating Solution

| Tris | 10 mM pH 9.2 |
|---|---|
| BSA (bovine serum albumin) | 1.0% |
| PEG (average molecular weight: 20,000) | 0.1% |

Tris Buffer Solution

| Tris | 10 mM pH 9.2 |
|---|---|

Suspending Solution

| Tris | 200 mM pH 9.2 |
|---|---|

Sample:
Plasmas (n=21) from humans who gave informed consent were used.

4) Assay Using Test Instrument

Correlation with the existing method (latex method) was confirmed using sera (n=21) from humans who gave informed consent.

For the correlation confirmation, the assay was conducted using N-Assay LA CRP D-type (manufactured by Nittobo Medical Co., Ltd.) as the existing method and Hitachi automatic analyzer model 7180. Also, a calibration curve for the dry reagent was prepared using control plasma having a known CRP concentration.

2. Results

Figure 6:
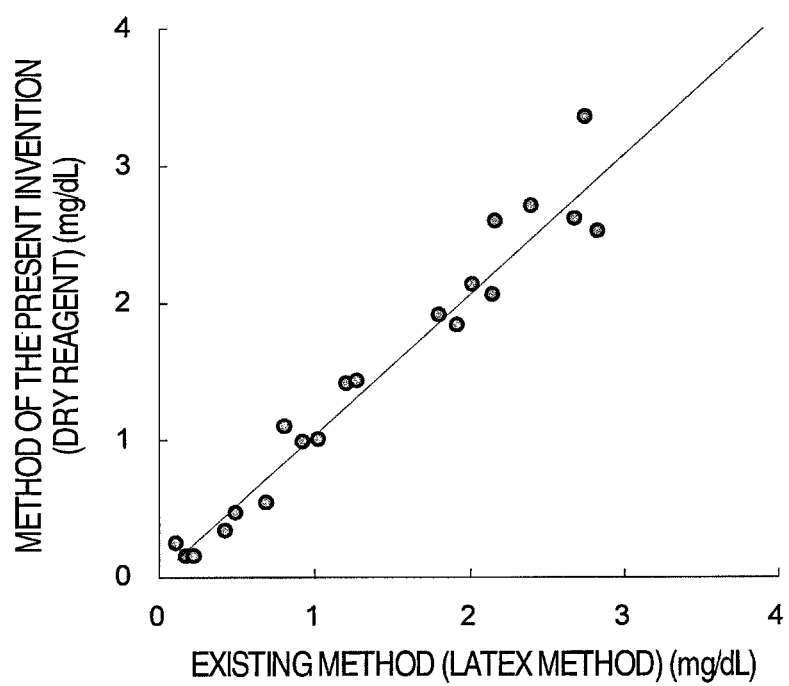
FIG. 6 is a diagram showing the correlation of human CRP assay between the assay method of the present invention based on dry chemistry using a palladium colloid and an assay method based on the existing liquid reagent method.

Correlation was confirmed by plotting the existing method on the X-axis and the method of the present invention on the Y-axis. As shown in FIG. 6, the favorable results of Y=1.0207X+0.252 with a correlation coefficient of 0.9817 were obtained. This shows that the assay method of the present invention can accurately assay human CRP using a palladium colloid.

Comparative Example 1

Assay of Human CRP Using Substance Other than Noble Metal Colloid

An anti-human CRP antibody-sensitized latex (polystyrene polymer) reagent was prepared using latex instead of a noble metal colloid and used in the same experiment as in Example 1.

The latex reagent failed to produce concentration-dependent absorbance because absorbance formed by turbidity during photometry was inhibited by the scattered light of the latex. In addition, due to the poor dispersibility or diffusibility of the latex reagent, it was impossible to completely disperse or diffuse the particles in a dry state after sample supply.

The dispersibility or diffusibility problem also arose even when colored latex particles, which hardly caused scattered light, was used. These particles were unable to be adapted as a dry reagent.

Alternatively, in the study of a dry reagent using a TIA method, the obtained change in absorbance was exceedingly small and a low-concentration protein such as CRP was unable to be quantified.

INDUSTRIAL APPLICABILITY

The test instrument of the present invention and the method for assaying an analyte using the same are capable of accurately assaying an analyte in a liquid sample by dry chemistry using the convenient test instrument. Furthermore, the test instrument and the assay method of the present invention are capable of assay based on absorbance in the visible region and as such, can be applied to an apparatus using a general-purpose visible spectrophotometer and can accurately assay an analyte in a short time. The test instrument and the assay method of the present invention are suitable for the POCT field.

REFERENCE SIGNS LIST

1 First plate
2 Printing surface 1
3 Printing surface 2
4 Second plate
5 Dry reagent 1
6 Intermediate plate
7 Supply unit
8 Stopper
9 Membrane
10 Channel
11 Reaction chamber
12 Dry reagent 2

The invention claimed is:

1. A test instrument for spectrophotometrically and quantitatively assaying an analyte in a liquid sample by aggregation assay using dry particles of noble metal, the test instrument comprising:
   a reaction chamber;
   reagents attached in a dry state to at least a portion of a surface constituting the reaction chamber, wherein the reagents include
   (i) dry particles of noble metal sensitized with a partner specifically binding to the analyte; or
   (ii) a partner specifically binding to the analyte and dry particles of noble metal sensitized with the same substance as the analyte,
   wherein said noble metal particles are capable of forming a noble metal colloid upon contact with the liquid sample, for assaying the analyte by the aggregation assay using a noble metal colloid and the particle size of the noble metal colloid is 20 to 150 nm;
   a sample supply unit for supplying the liquid sample;
   a channel for transporting the liquid sample supplied to the sample supply unit into the reaction chamber; and,
   a stopper which covers the sample supply unit after the liquid sample is supplied to the sample supply unit,
   wherein, by pressurizing the stopper, the test instrument is capable of generating a pressure difference between the sample supply unit and the reaction chamber such that the liquid sample supplied to the sample supply unit is transported into the reaction chamber via the channel and contacted with the reagent attached in a dry state to disperse the reagent in the liquid sample.

2. The test instrument according to claim 1, wherein the surface constituting the reaction chamber comprises:
   a first planar surface,
   a second planar surface facing the first planar surface, and
   a third surface being in contact with both the first planar surface and the second planar surface and defining a space between the first planar surface and the second planar surface,
   wherein
   the reagents include said reagent (i).

3. The test instrument according to claim 1, wherein the surface constituting the reaction chamber comprises:
   a first planar surface,
   a second planar surface facing the first planar surface, and a third surface being in contact with both the first planar surface and the second planar surface and defining a space between the first planar surface and the second planar surface, wherein the reagents include said reagent (ii);

said partner specifically binding to the analyte is attached in a dry state to the first planar surface; and said dry particles of noble metal are attached to the second planar surface.

4. The test instrument according to claim 1, wherein the noble metal particles are gold particles or palladium particles.

5. The test instrument according to claim 1, wherein the channel and the reaction chamber are connected to an outside of the test instrument via an air-permeable and liquid-impermeable porous membrane.

6. The test instrument according to claim 1, wherein the liquid sample is a biological sample, and the analyte is a biogenic component.

7. The test instrument according to claim 1, further comprising, between the sample supply unit and the channel, a membrane for separating a solid from the liquid sample.

8. The test instrument according to claim 1, wherein the average particle size of the noble metal colloid prior to aggregation is 50 nm.

9. The test instrument according to claim 1, wherein the dry particles are a noble metal colloid.

10. The test instrument according to claim 9, wherein the noble metal is selected from the group consisting of gold, silver, palladium and platinum.

11. The test instrument according to claim 10, wherein the noble metal is gold.

12. The test instrument according to claim 10, wherein the noble metal is platinum.

13. The test instrument according to claim 9, wherein the dry particles are an anti-human CRP antibody-sensitized gold colloid.

14. The test instrument according to claim 9, wherein the dry particles comprise an anti-human CRP antibody-sensitized gold colloid.

15. The test instrument according to claim 14, wherein dry particles further comprise sorbitol and a surfactant.

16. An apparatus for assaying an analyte in a liquid sample, comprising a test instrument according to claim 1 in combination with a visible spectrophotometer for irradiating the reaction chamber with light and reading transmitted light or reflected light.

* * * * *